United States Patent
Cho et al.

(10) Patent No.: US 8,859,236 B2
(45) Date of Patent: Oct. 14, 2014

(54) MICROORGANISM WITH IMPROVED PRODUCTION OF 5'-XANTHOSINE MONOPHOSPHATE AND 5'-GUANINE MONOPHOSPHATE, AND PRODUCTION METHOD OF 5'-XANTHOSINE MONOPHOSPHATE AND 5'-GUANINE MONOPHOSPHATE USING SAME

(75) Inventors: Jin Man Cho, Seoul (KR); Jin Nam Lee, Seoul (KR); Hye Won Kim, Gyeonggi-do (KR); Ji Hye Lee, Gyeonggi-do (KR); Nan Young Yoon, Seoul (KR); Kwang Woo Lee, Seoul (KR); Yoon Seok Oh, Gyeonggi-do (KR); Jang Hee Park, Gyeonggi-do (KR)

(73) Assignee: CJ Cheiljedang Corporation, Seoul (KR)

( * ) Notice: Subject to any disclaimer, the term of this patent is extended or adjusted under 35 U.S.C. 154(b) by 98 days.

(21) Appl. No.: 13/635,801

(22) PCT Filed: Mar. 17, 2011

(86) PCT No.: PCT/KR2011/001866
§ 371 (c)(1),
(2), (4) Date: Nov. 26, 2012

(87) PCT Pub. No.: WO2011/115439
PCT Pub. Date: Sep. 22, 2011

(65) Prior Publication Data
US 2013/0095529 A1    Apr. 18, 2013

(30) Foreign Application Priority Data
Mar. 19, 2010 (KR) .................. 10-2010-0024929

(51) Int. Cl.
| C12Q 1/00 | (2006.01) |
| C12Q 1/26 | (2006.01) |
| C12N 15/77 | (2006.01) |
| C12N 9/26 | (2006.01) |
| C12P 19/32 | (2006.01) |
| C12N 9/06 | (2006.01) |

(52) U.S. Cl.
CPC ................. C12N 15/77 (2013.01); C12P 19/32 (2013.01); C12Y 105/99008 (2013.01); C12N 9/0026 (2013.01)
USPC ..................... 435/88; 435/252.32; 435/320.1; 435/69.1

(58) Field of Classification Search
CPC combination set(s) only.
See application file for complete search history.

(56) References Cited

U.S. PATENT DOCUMENTS
2002/0098552 A1    7/2002  Livshits et al.

FOREIGN PATENT DOCUMENTS

| EP | 1 029 926 A1 | 8/2000 |
| KR | 10-1991-0018061 | 10/1991 |
| KR | 10-1993-0008130 | 5/1993 |
| KR | 10-2001-0000513 | 1/2001 |
| KR | 10-2002-0057470 | 7/2002 |
| KR | 10-2007-0056491 | 6/2007 |
| KR | 10-2008-0006537 | 1/2008 |
| KR | 10-2009-0080654 | 7/2009 |

OTHER PUBLICATIONS

Office Action issued in Chinese Patent Application No. 201180019964.5, dated Sep. 30, 2013.
Bott et al., "The Respiratory Chain of *Corynebacterium Glutamicum*," *Journ. of Biotechnology*, vol. 104, pp. 129-153 (2003).
Mani et al., "Altered Levels of Proline Dehydrogenase Cause Hypersensitivity to Proline and Its Analogs in *Arabidopsis*," *Plant Physiology*, vol. 128, pp. 73-83 (2002).

*Primary Examiner* — Kagnew H Gebreyesus
(74) *Attorney, Agent, or Firm* — Foley & Lardner LLP

(57) ABSTRACT

The present invention relates to a microorganism with improved production of 5'-xanthosine monophosphate and 5'-guanine monophosphate, and more specifically, to a *Corynebacterium* sp. microorganism having increased proline dehydrogenase activity compared with an intrinsic activity thereof, a method for producing 5'-xanthosine monophosphate or 5'-guanine monophosphate from the culture medium obtained by culturing the transformed microorganism, and a use of the microorganism for production of 5'-xanthosine monophosphate or 5'-guanine monophosphate.

10 Claims, 1 Drawing Sheet

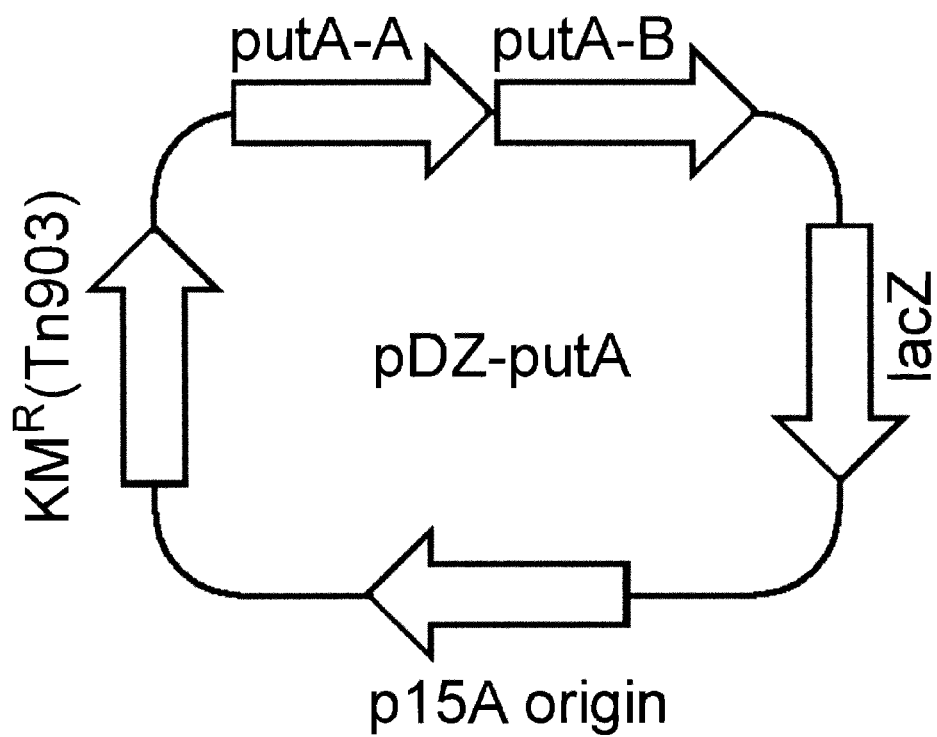

SEQUENCE LISTING

```
<160> NUMBER OF SEQ ID NOS: 7

<210> SEQ ID NO 1
<211> LENGTH: 32
<212> TYPE: DNA
<213> ORGANISM: Artificial Sequence
<220> FEATURE:
<223> OTHER INFORMATION: forward primer for putA-A

<400> SEQUENCE: 1
cccaagcctt gagcgcgtcg gtcactcaac ta                              32

<210> SEQ ID NO 2
<211> LENGTH: 19
<212> TYPE: DNA
<213> ORGANISM: Artificial Sequence
<220> FEATURE:
<223> OTHER INFORMATION: reverse primer for putA-A

<400> SEQUENCE: 2
cagccaatct tgcagccaa                                             19

<210> SEQ ID NO 3
<211> LENGTH: 21
<212> TYPE: DNA
<213> ORGANISM: Artificial Sequence
<220> FEATURE:
<223> OTHER INFORMATION: forward primer for putA-B

<400> SEQUENCE: 3
tgagcgtcgg tcactcaact a                                          21

<210> SEQ ID NO 4
<211> LENGTH: 28
<212> TYPE: DNA
<213> ORGANISM: Artificial Sequence
<220> FEATURE:
<223> OTHER INFORMATION: reverse primer for putA-B

<400> SEQUENCE: 4
cgggatccca gccaatcttg cagtccaa                                   28

<210> SEQ ID NO 5
<211> LENGTH: 21
<212> TYPE: DNA
<213> ORGANISM: Artificial Sequence
<220> FEATURE:
<223> OTHER INFORMATION: forward primer of putA for PCR

<400> SEQUENCE: 5
cgaactacgt ggcacagttt g                                          21

<210> SEQ ID NO 6
<211> LENGTH: 20
<212> TYPE: DNA
<213> ORGANISM: Artificial Sequence
<220> FEATURE:
```

<223> OTHER INFORMATION: reverse primer of putA for PCR

<400> SEQUENCE: 6
agcaggccat taaaacgacc                                                    20

<210> SEQ ID NO 7
<211> LENGTH: 3435
<212> TYPE: DNA
<213> ORGANISM: Corynebacterium ammoniagenes
<220> FEATURE:
<221> NAME/KEY: gene
<222> LOCATION: (1)..(3435)
<223> OTHER INFORMATION: putA gene

<400> SEQUENCE: 7

| | | | | | |
|---|---|---|---|---|---|
| atgactactg | ccgcacatac | tcgcctaact | gaatctaatg | acgtcgaagc | cgtcgttgat | 60 |
| gccgctgccc | agcgcgcacg | caagtggctc | gcggtcactg | aaggtgagca | cgatgcttcc | 120 |
| tcagaacaac | tagctgacct | gcttcgtgat | gaagacggtg | ttgctttcac | catggacttt | 180 |
| gtcgaccgcg | ttatgcgccc | ggaagatgac | aaagtagcgg | ccaaggcgct | taaggccatg | 240 |
| accaataaat | tcgatccttc | gtttctgggt | cgttttaatg | gcctgctggt | cggtatgggc | 300 |
| ggattcttcg | gccctatttt | gcccaacctg | gttatgcctt | ggcgcggtt | cgcatgcgg | 360 |
| caaatggtcg | gccacctggt | gctcgatgcc | gaatccgaca | agctgaataa | gactttggct | 420 |
| aaagctgccg | agtccggtga | acaattgaat | ctcaacctgc | tgggtgaggc | ggtgctgggc | 480 |
| gaagatgaag | cccgctcccg | cgctgagcgc | accctcgcac | tgattcgtaa | tccgctggtc | 540 |
| acctatgttt | ctgtgaaggc | ctcctccatg | gtcgcgcagc | taaaccctg | ggatattgaa | 600 |
| ggttcgctgg | agcgcctcaa | agagcgtttg | cttccgcttt | acgatgaagc | cgcgaagcgc | 660 |
| tctcccaacg | tctttatcaa | cttagacatg | gaggaatatc | atgacctgca | cctgaccatc | 720 |
| cggcttttca | agaaaattct | ggccgaccca | agttcaagg | atctagaagt | aggcattgtt | 780 |
| ttgcaggctt | atctgccaga | taccttcgag | tgcctggtgg | atttggcgga | atttgcgcaa | 840 |
| gagcgcgtgg | cccagggcgg | ggcgccgatt | aagattcgct | tcgtgaaagg | cgcgaatctg | 900 |
| tccatggagc | atgtccaagg | cgaggtacac | ggctggcaag | tcgcgacgta | cttgagtaaa | 960 |
| gacgaggtcg | atgccaacta | ctaccgcctg | ctggattata | ttttgcgccc | gcagttcgag | 1020 |
| ggagccgtgc | gcattggtgt | tgctacacat | aacctctta | ccgcaggctt | ggcctatgag | 1080 |
| ctgggtaaaa | agcgcgacgt | actgtccatg | atggactcgg | agatgctaca | gggcatgtcg | 1140 |
| ccatcgcagc | aggctgcggt | acgcgagatg | tttggccgcc | agattctcta | caccccagtc | 1200 |
| gtgcacatgg | aagacttcga | tgtcgcggtg | tcttacttgg | tgcgccgttt | ggaagaaaac | 1260 |
| tctgccgagc | agaacttcct | ttatgctttg | tttgcgccag | atgtggcaga | taatgaaggg | 1320 |
| cttacgccgc | tgcagaagca | ggaaaaggtc | ttccgcgagg | ctgttgctaa | tcgttgggac | 1380 |
| gttttttgccg | gccgcgccg | cacccaggac | cgtttaacgg | aagaaggtgg | gcgtcaagct | 1440 |
| gccaagactg | gccgctttgt | caatgagcca | gatactgacc | cagccttgga | agacaaccgc | 1500 |
| gcctgggcac | tggaggcatt | ggctaatgat | ccaggcgagc | acgggatcac | cgaggtcacc | 1560 |
| gacacagagg | ctgtaaacca | ggctgtggcc | aaagcccagg | agttgggcgc | tcagtggggc | 1620 |
| gcaaagcctg | ccgatgaacg | cgccgcggtc | ctagaggcca | tcggtgatga | acttgcgcgc | 1680 |
| agccgcggca | agctagtcag | cgttgctgct | tatgaggcga | ataagaccgt | cacgcaaact | 1740 |
| gacccggaaa | tctctgaggc | catcgacttt | tgcgtctact | acgcgcattc | ggcacgtcag | 1800 |
| ctcgatgccg | cgcgttctca | gttcacccg | caccaggtca | ccgtggtgac | tccgccgtgg | 1860 |

-continued

```
aatttcccta tcgctattcc gaccggaggc atgatggcag cgctggcggc gggctcggcg    1920
gtcatcatca agccggcacc gcaggtggtg cactgcgcga agaccgtcgt cggtgccatt    1980
cacactgcac ttgaagcgca gggcttggat aaggacttag tccagctggt ttacaccgat    2040
gaaggtgatg ccggcaaggc cctgatctcg catacggatg tcgataatgt gattctcacc    2100
ggcgcttccg ataccgggca gctatttcgc tcctggcgcc ccgagatgaa cttatctgcg    2160
gaaacctccg gaaagaatgc gctgattatt accccagcag cagatcccga cctggccatc    2220
gcagatctct acgactcagc gttcggccac tctggccaaa agtgctcggc agcttccttg    2280
gttatcttcg tcggcgctgc cggcaagtcg gatcgcctac gcaatcagct tctcgatgcc    2340
gtccgcactc tcaaagtcgg ccccggcttc gaaatccaga ccaccatgaa tggcttggtt    2400
gagccgccga gcgagaaact gctgcgcggt ctaacccagt tggacccggg cgagaagtgg    2460
ctgattaagc cggaaaagct caacgaagaa ggcaccctgt ggtccctgg cgtgcgcgat    2520 aatgtgcagc ctggttcgtg gtaccacctc aacgagtgct tcggaccggt cctaggcatc    2580
atgcacgctg aaaccctgga agaggccgtc gaatggcaaa attccacggg ctttgggctc    2640
acgggcggca ttcattcgct tgacgatgaa gaactgcgct actggatcga caacgtcgaa    2700
gtcggcaatg cttatgtcaa ccgcgggatt accggcgcga ttgtgcagcg ccagtccttc    2760
ggtggctgga agaaatccgt catgggacca ggcgcaaaag ccggcggtcc gaactacgtg    2820
gcacagtttg gctcctggga agacggtgac ctgaacccgg tcgatgtgga tatcgcgccg    2880
cagatcgtcg cgtggttacg cgaggtggca tcgttaagcg aagctgatac cgcctggctc    2940
tggcgcgccg ctgagctgga tcaattggcg tggcagacgg agtttgggcg cgagcatgac    3000
cgcaccggat tggtgtctga ggcgaatatc ttccgctacc gcccgctgct ggatgtcttg    3060
cgtatccgcg taggtgctgg ataccagttg cgcgacgttt tacgccagca acttgcagcg    3120
ctgattacgg gaactgaaat ccggatttct gcgcctgccg agattgctgc ggagctaccg    3180
gttaatgtca cggtacagtc cgccgcggaa tttgctgagg aggtcgcgaa tgcagaatcg    3240
gcccgaattc gcgcactagg cgaagtcgag ccggaggttt atgaggctgc ggtgaaatct    3300
aactcggtag ttctcgcgca gcccgtgctt gccgatggcc gccgcgagct actgccttat    3360
cttctcgagc aggcggtcac cgtgaccatg caccgcttcg gaattatccg ttcggtagct    3420
ggcattaagc gctaa                                                    3435
```

MICROORGANISM WITH IMPROVED PRODUCTION OF 5'-XANTHOSINE MONOPHOSPHATE AND 5'-GUANINE MONOPHOSPHATE, AND PRODUCTION METHOD OF 5'-XANTHOSINE MONOPHOSPHATE AND 5'-GUANINE MONOPHOSPHATE USING SAME

BACKGROUND OF THE INVENTION

1. Field of the Invention

The present invention relates to a *Corynebacterium* microorganism having increased proline dehydrogenase activity compared to its endogenous activity, a method for producing 5'-xanthosine monophosphate or 5'-guanine monophosphate from a culture solution by culturing the transformed microorganism, and use of the microorganism for the production of 5'-xanthosine monophosphate or 5'-guanine monophosphate.

2. Description of the Related Art

5'-Guanine monophosphate (GMP) is a food additive widely used as a flavor enhancer, together with inosine monophosphate (IMP). GMP is known to impart a mushroom-like taste on its own, and to increase the taste intensity of monosodium glutamate (MSG) when combined therewith. It is often used in combination with IMP.

Examples of the methods for the preparation of GMP known thus far comprise (1) the enzymatic degradation of RNA (Ribonucleic Acid) extracted from yeast cells, (2) direct microorganism fermentation to GMP, (3) microorganism fermentation to guanosine, followed by chemical phosphorylation, (4) microorganism fermentation to guanosine, followed by enzymatic phosphorylation, (5) microorganism fermentation to xanthosine 5'-monophosphate (XMP), followed by conversion into GMP by a *Corynebacterium* strain, and (6) microorganism fermentation to XMP, followed by conversion of XMP into GMP by *Escherichia coli*. Among them, method (1) has the difficulties of limited material supply and being economically non-beneficial, and method (2) suffers from the disadvantage of being of low yield due to the membrane permeability of GMP. Thus, the other methods are widely used in industrial applications.

In the above described methods, when GMP is produced by conversion of XMP into GMP, it is required to increase XMP productivity or to continuously supply ATP that is used as a cofactor during GMP conversion. To increase XMP productivity, the conventional methods produced guanosine or XMP-resistant microorganisms by mutation. For example, Korean Patent Application No. 10-1991-018061 discloses an XMP aminase-inactive strain capable of producing XMP in high yield, which is semi-auxotrophic for adenine and guanine, tolerant of guanosine analogs and very susceptible to lysozyme, an enzyme which destroys cell walls. Further, Korean Patent Application No. 10-2001-000513 discloses a strain of *Corynebacterium ammoniagenes* that is able to directly accumulate XMP at high concentration in a culture medium and a method of producing XMP using the same, in which the strain is prepared by irradiating the mother microorganism with UV light, treating with the mutagen N-methyl-N'-nitro-N-nitrosoguanidine (NTG), and selecting a mutant tolerant of norvaline, an analog of valine which affects the biosynthesis of XMP. Furthermore, Korean Patent Application No. 10-2008-006537 describes a method of increasing XMP yield in which purN and purH genes involved in the biosynthesis of XMP are modified.

As mentioned above, for the conversion of XMP into GMP, it is critical to supply ATP which is used as a cofactor during GMP conversion. Most of the ATP used in the conversion of XMP to GMP is supplied from an XMP-producing strain. In the conversion approach, xylene increases the membrane permeability of ATP and XMP, and addition of xylene to the medium allows ATP and XMP to penetrate into a GMP-producing strain, followed by the conversion of XMP into GMP. Therefore, the approach to GMP production takes the strategy of increasing ATP productivity.

The conversion from XMP into GMP is represented by the following reaction formula:

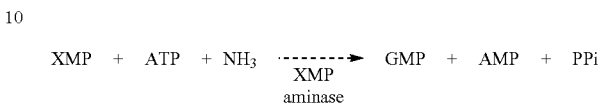

That is, a continuous supply of ATP, serving as a cofactor, is essential for the conversion process in which XMP is primarily produced and then converted into GMP by addition of an enzyme or microorganism having XMP aminase activity to the culture medium comprising XMP and a microorganism. Thus, it is very important to enhance ATP productivity of the XMP-producing strain. The AMP produced in the conversion process is reused as a substrate for ATP production. In fact, adenine-based nucleotides are recycled for the production of ATP in the conversion process.

Hence, improvement of XMP productivity is necessary for the high production yield of GMP, and XMP productivity can be improved by increasing ATP productivity. Based on this background, the present inventors have made many efforts to develop a method for increasing ATP productivity. As a result, they found that enhanced activity of proline dehydrogenase improves production yields of XMP and GMP by increasing ATP production.

Therefore, the present inventors identified a gene responsible for the improvement of XMP production yield, designed a vector comprising the gene, and prepared a microorganism of the genus *Corynebacterium* transformed with the vector, and they found that XMP or GMP can be produced from the microorganism in a high yield, thereby completing the present invention.

SUMMARY OF THE INVENTION

An object of the present invention is to provide a *Corynebacterium* microorganism for producing 5'-xanthosine monophosphate or 5'-guanine monophosphate, having increased proline dehydrogenase activity compared to its endogenous activity.

Another object of the present invention is to provide a method for producing 5'-xanthosine monophosphate or 5'-guanine monophosphate from a culture solution by culturing the microorganism.

Still another object of the present invention is to provide use of the microorganism for the production of 5'-xanthosine monophosphate or 5'-guanine monophosphate.

BRIEF DESCRIPTION OF THE DRAWINGS

FIG. 1 is a schematic diagram showing the structure of a pDZ-putA vector that is prepared by cloning a putA gene into a pDZ vector.

DETAILED DESCRIPTION OF THE PREFERRED EMBODIMENTS

In one aspect to achieve the above objects, the present invention relates to a *Corynebacterium* microorganism having increased proline dehydrogenase activity compared to its endogenous activity.

Preferably, the present invention provides a *Corynebacterium* microorganism that has increased praline dehydrogenase activity compared to its endogenous activity to show improved productivities of 5'-xanthosine monophosphate (XMP) and 5'-guanine monophosphate (GMP).

As used herein, the term "proline dehydrogenase" is proline dehydrogenase/delta-1-pyrroline-5-carboxylate dehydrogenase, and is known to be involved in alanine, aspartate and glutamate metabolic pathways, arginine and proline metabolic pathways. The present invention relates to a microorganism showing improved production yields of XMP and GMP by increasing activity of the corresponding enzyme.

As used herein, the term "endogenous activity" refers to the intrinsic enzyme activity in a wild-type microorganism, and the term "increasing compared to endogenous activity" means increased enzyme activity compared to the intrinsic activity. The increased enzyme activity of the present invention comprises an improve in an endogenous activity of a gene product, amplification of the endogenous gene by internal or external factors, an increase in the gene copy number, or an increase in the activity by introduction of a foreign gene, as well as an increase in the activity of the enzyme itself to achieve effects beyond the intrinsic functions. The increased enzyme activity may be achieved by any method known in the art without limitation, for example, an increase in the copy number of gene, replacement or modification of a promoter, and an increase in the enzymatic activity by mutation, but the method is not limited to these examples.

The proline dehydrogenase whose activity is increased by the present invention may be encoded by the putA gene of *Corynebacterium*. Any derivative or analog may be comprised in the present invention, as long as it is biologically identical or corresponds to the gene. Any gene is comprised in the present invention, as long as it shows a biological activity that is substantially identical or similar to that of the putA gene, and has preferably 70% or higher, more preferably 80% or higher, even more preferably 90% or higher, even far more preferably 95% or higher and most preferably 98% or higher homology with the sequence of the putA gene. Preferably, the putA gene of the present invention may be encoded by the nucleotide sequence of SEQ ID NO. 7. When the copy number of gene is increased by internal or external factors, the copy number to be increased may be readily determined by those skilled in the art according to need and purpose. The amplification of the endogenous gene can also be conducted using a method known in the art, for example, by cultivation under a suitable selection pressure, but the amplification method of the endogenous gene is not limited to this example.

In a preferred Example of the present invention, a vector carrying a gene coding for proline dehydrogenase is introduced into a *Corynebacterium* microorganism so as to generate a transformed microorganism with an enhancement over the endogenous activity.

The "*Corynebacterium* microorganism" of the present invention may be any strain without limitation, as long as it is known in the art and belongs to the genus *Corynebacterium*. Preferably, examples thereof may comprise *Corynebacterium ammoniagenes, Corynebacterium glutamicum, Brevibacterium flavum*, and *Brevibacterium lactofermentum*, but the type of the microorganism of the genus *Corynebacterium* useful in the present invention is not limited to these examples. In detail, the *Corynebacterium* microorganism comprise *Corynebacterium ammoniagenes* ATCC6872, *Corynebacterium thermoaminogenes* FERM BP-1539, *Corynebacterium glutamicum* ATCC 13032, *Corynebacterium glutamicum* R, *Brevibacterium flavum* ATCC 14067, *Brevibacterium lactofermentum* ATCC 13869 and derivatives thereof. Preferred is *Corynebacterium ammoniagenes* KCJ-1346 transformed from *Corynebacterium ammoniagenes* KCCM 10530. Specifically, the strain of the present invention may be a strain having two or more copies of putA gene incorporated into the genome of *Corynebacterium ammoniagenes* KCCM10530, resulting from the introduction thereinto of a vector having the cleavage map of FIG. 1 and the homologous recombination of at least two copies of putA gene with the endogenous gene by cultivation of the microorganism transformed with the vector.

As used herein, the term "5'-xanthosine monophosphate (XMP)" is an intermediate in nucleic acid biosynthesis and is of physiological significance in animals and plants. Also, it finds applications in a variety of fields comprising the food industry, the pharmaceutical industry and the medical industry. It is a food additive used as a nucleic acid-based flavor enhancer in synergy with monosodium glutamate. XMP is an intermediate in the purine nucleotide biosynthetic metabolism, and is an important raw material for the production of 5'-guanine monophosphate (GMP). Preferably, the transformed microorganism having improved XMP productivity was prepared and cultured to obtain XMP from the culture solution. As a result, it was found that the transformed microorganism showed approximately 4.5% higher XMP productivity than the conventional microorganisms, and thus XMP production could be increased by using the microorganism.

As used herein, the term "5'-guanine monophosphate (GMP)" is one of the nucleotides, composed of guanosine and phosphate. It is found in nucleic acids, and divided into 3 types of 5'-, 3'- and 2'-form according to the position. In the present invention, 5'-guanosine monophosphate is produced as a colorless needle-shaped crystal, and exists in free form within the body. It has a molecular formula of $C_{10}H_{14}N_5O_8P$. Its sodium salts provide the taste of shiitake mushroom and thus are used as chemical seasonings. GMP is one of nucleic acid-based flavor enhancers to provide the taste of mushroom. Preferably, the present invention identified a method for producing 5'-guanine monophosphate in a high yield using the transformed microorganism, and it was found that the method showed approximately 7% increased GMP concentration, compared to the methods using the conventional microorganisms.

In the present invention, a vector comprising the putA gene was introduced to prepare a microorganism having improved proline dehydrogenase activity. With respect to the objects of the present invention, the vector may comprise a vector that comprises a gene having a biological activity substantially identical to that of the putA gene. It is apparent to those skilled in the art that the sequence of the gene showing a biological function substantially identical or similar to that of the putA gene may differ according to the type and characteristics of the transformed microorganism. Preferably, the present invention relates to a recombinant vector comprising the gene of SEQ ID NO. 7, which has the cleavage map of FIG. 1. The gene of SEQ ID NO. 7 of the present invention is a wild-type nucleotide sequence of the putA gene of *Corynebacterium*. The "putA gene" means a gene encoding proline dehydrogenase. In the case of *Corynebacterium glutamicum* ATCC13032, the gene showing the above function is known as accession number NC_006958, and its mRNA sequence is known as YP_224396.1.

In the preferred embodiment, the present invention provides a recombinant vector comprising the putA gene represented by SEQ ID NO. 7. The vector of the present invention may be any vector typically used in the art without limitation, as long as it is able to comprise the putA gene. The optimal vector is preferably selected according to the characteristics of a host to be used. Preferably, the vector is pDZ-putA. In the preferred Example of the present invention, the putA gene of SEQ ID NO. 7 was introduced into pDZ, thereby preparing the pDZ-putA vector (FIG. 1).

The transformed microorganism of the present invention may be prepared by an introduction of the putA gene into a host microorganism. Preferably, the putA gene is cloned into the vector, which is transformed into a cell.

The transformation may be performed by any method without limitation, and easily performed according to a typical method known in the art. As used herein, the term "transformation" means the introduction of DNA into a host cell so that the DNA can replicate, either as an extrachromosomal element, or by chromosomal integration, and is the artificial genetic alteration resulting from the uptake of foreign DNA. Typical transformation methods comprise $CaCl_2$ precipitation, a Hanahan method in which the effect of $CaCl_2$ precipitation is improved in combination with DMSO (dimethyl sulfoxide) as a reducing material, electroporation, calcium phosphate transfection, protoplast fusion, silicon carbide fiber-mediated transformation, agrobacterium-mediated transformation, polyethylene glycol (PEG)-mediated transformation, dextran sulfate, lipofectamine, and desiccation/inhibition-mediated transformation. Transformation with pDZ-putA of the present invention is not limited to these examples, but can be achieved using any method known in the art without limitation.

As used herein, the term "vector", which describes a recombinant vector capable of delivering a target protein into a suitable host cell, refers to a genetic construct that comprises essential regulatory elements to which a gene insert is linked in such a manner as to be incorporated into the chromosome of the host cell. Preferably, the recombinant vector comprising the putA gene of the present invention may be a recombinant vector comprising the cleavage map of FIG. 1. In the preferred Example of the present invention, the vector is introduced into *Corynebacterium ammoniagenes* KCCM10530 by the transformation method, which is then cultured in a selective medium to allow replacement of the endogenous gene by two copies of the putA gene through homologous recombination, resulting in insertion of two copies of the putA gene into the chromosome. As a result, a novel transformed microorganism was, designated as KCJ-1346, generated by the transformation of *Corynebacterium ammoniagenes*, which was deposited with accession number KCCM11068P at an International Depository Authority, the Korean Culture Center of Microorganisms (KCCM, 361-221, Yurim B/D, Hongie-1-dong, Seodaemun-gu, Seoul, Korea) on Feb. 24, 2010.

According to the present invention, XMP or GMP can be produced in the culture media in a high yield by direct fermentation of the above described transformed microorganism. Preferably, the microorganism used in the method is a microorganism having improved activity of proline dehydrogenase, and the putA gene of the vector is inserted into the chromosome of the host microorganism, thereby increasing the production of XMP and GMP. Preferably, the microorganism used in the production method may be a microorganism having accession number KCCM11068P.

In another aspect, the present invention relates to a method for producing 5'-xanthosine monophosphate or 5'-guanine monophosphate from a culture solution by culturing the microorganism according to the present invention.

Preferably, the present invention provides a method for producing XMP, comprising the step of culturing the strain transformed with the vector comprising the putA gene so as to obtain XMP, and also provides a method for producing GMP, comprising the steps of (a) culturing the strain transformed with the vector comprising the putA gene; (b) adding XMP aminase to the culture solution of the strain obtained in step (a); and (c) obtaining GMP from the culture solution of step (b). More preferably, provided is a method for producing XMP by directly accumulating XMP in the culture media in a high yield through direct fermentation of the deposited microorganism. Additionally, the conversion process is performed by addition of an enzyme or microorganism having XMP aminase activity, preferably, *E. coli* to the culture medium comprising XMP and the transformed microorganism, and subsequently, GMP is separated and purified from the culture medium so as to obtain GMP.

The medium used in the present invention may be any medium typically used in the art without limitation. Preferably, the medium contains glucose as a carbon source and optionally a proper amount of various other carbon sources. For use in the cultivation, a medium must meet requirements for the growth of the microorganism. Culture media for *Corynebacterium* strain are known in the art (e.g., Manual of Methods for General Bacteriology. American Society for Bacteriology. Washington D.C., USA, 1981). Examples of the carbon sources to be used may comprise sugars and carbohydrates such as glucose, galactose, saccharose, arabinose, maltose, xylose, trehalose, ribose, lactose, fructose, maltose, starch, and cellulose, oils and lipids such as soybean oil, sunflower oil, castor oil, and coconut oil, fatty acids such as palmitic acid, stearic acid, and linolenic acid, alcohols such as glycerol and ethanol, and organic acids such as acetic acid. These carbon sources may be used individually or in combination. Examples of the nitrogen sources to be used may comprise organic nitrogen sources such as peptone, yeast extract, beef extract, malt extract, corn steep liquor, soybean, and urea, and inorganic nitrogen sources such as ammonium sulfate, ammonium chloride, ammonium phosphate, ammonium carbonate and ammonium nitrate. These nitrogen sources may be also used individually or in combination. Examples of the phosphorus sources to be used in the medium may comprise potassium dihydrogen phosphate or dipotassium hydrogen phosphate, or corresponding sodium salts. In addition, the culture medium may comprise metal salts such as magnesium sulfate and iron sulfate required for the growth. Essential elements such as amino acids and vitamins or suitable precursors may be further comprised in addition to the above materials. These materials may be properly added to the medium in a batch manner or continuous manner during the cultivation.

During the cultivation, pH of the culture medium may be properly adjusted by basic compounds such as sodium hydroxide, potassium hydroxide, and ammonia, or acid compounds such as phosphoric acid and sulfuric acid. An antifoaming agent such as fatty acid polyglycol ester may be used to prevent the generation of bubbles. The medium may be aerated with oxygen or oxygen-containing gas (e.g., air) to maintain an aerobic condition or with nitrogen, hydrogen or carbon dioxide gas to maintain anaerobic and microaerobic conditions. Temperature of the culture is usually maintained at 20° C. to 45° C., and preferably at 30° C. to 35° C. or at 35° C. to 37° C. Cultivation may be continued until the maximum amount of the desired material is obtained, and preferably it may be achieved within 10 to 160 hours.

The XMP or GMP may be secreted into the culture medium or remain within the cell. The method for producing XMP or GMP of the present invention comprises the step of recovering XMP or GMP from the cells or the culture medium. The method of recovering XMP or GMP from the cells or the culture media is widely known in the art. The method of recovering XMP or GMP may comprise filtration, anionic exchange chromatography, crystallization, and HPLC, but is not limited thereto.

In still another aspect, the present invention relates to use of the microorganism according to the present invention for the production of 5'-xanthosine monophosphate or 5'-guanine monophosphate.

The *Corynebacterium* microorganism for producing 5'-xanthosine monophosphate or 5'-guanine monophosphate, which has increased proline dehydrogenase activity compared to its endogenous activity, is able to produce XMP or GMP in a high yield owing to improved activity of proline dehydrogenase, thereby being effectively used for the production of 5'-xanthosine monophosphate or 5'-guanine monophosphate.

Hereinafter, the present invention will be described in more detail with reference to Examples. However, these Examples are for illustrative purposes only, and the invention is not intended to be limited by these Examples.

Example 1

Cloning of the XMP-Producing Strain *Corynebacterium ammoniagenes* KCCM10530-Derived putA and Construction of Recombinant Vector (pDZ-putA) for Genomic Incorporation In this Example, a pDZ vector disclosed in Korean Patent Publication No. 10-2007-94433 was used to perform genomic incorporation of the gene. For incorporation of the gene into *Corynebacterium* genome using the pDZ vector, a pDZ vector comprising the insert sequence at both ends was constructed, because a sequence having homology with a region incorporated into the chromosome must be comprised in the pDZ vector.

In this Example, for amplification of the putA gene, the nucleotide sequence of the putA gene (NCBI ID_3344496) was obtained based on the NIH GenBank. Based on the sequence, two pairs of primers (SEQ ID NOs. 1 to 4) were synthesized.

PCR was performed in the presence of the high-fidelity DNA polymerase PfuUltra™ (Stratagene, USA) using the genome of *Corynebacterium* KCCM10530 as a template and the oligonucleotides of SEQ ID NOs. 1 to 4 as primers under the PCR conditions of 25 cycles consisting of denaturation at 95° C. for 30 seconds; annealing at 55° C. for 30 seconds; and polymerization at 68° C. for 2 minutes. The PCR products thus obtained were two copies of the putA gene (putA-A, putA-B), each 4.4 kb long, which were amplified using two primer sets of SEQ ID NOs. 1 and 2, and SEQ ID NOs. 3 and 4, respectively.

```
SEQ ID NO. 1:   CCCAAGCCTTGAGCGCGTCGGTCACTCAACTA
SEQ ID NO. 2:   CAGCCAATCTTGCAGCCAA
SEQ ID NO. 3:   TGAGCGTCGGTCACTCAACTA
SEQ ID NO. 4:   CGGGATCCCAGCCAATCTTGCAGTCCAA
```

After being treated with restriction enzymes (putA-A: HindIII, putA-B: BamHI), the PCR products putA-A, putA-B were inserted into the pDZ vector which was previously treated with HindIII and BamHI, through the three-piece junction. Finally, a recombinant pDZ-putA vector in which two copies of the putA gene were cloned in tandem was obtained. FIG. 1 is a schematic diagram showing the structure of the pDZ-putA vector for incorporation into *Corynebacterium* genome.

Example 2

Generation of putA-Inserted Strain

The pDZ-putA vector construct was transformed into the KCCM10530 strain and subjected to secondary homologous recombination with the genome to insert one copy of putA gene at a position adjacent to the putA gene on the genome, as described in Example 1. Thus, a XMP-producing *Corynebacterium ammoniagenes* KCJ-1346, which had two copies of the putA gene on the genome thereof, was obtained. The novel microorganism, designated as KCJ-1346, was deposited with accession number KCCM11068P at an International Depository Authority, the Korean Culture Center of Microorganisms (KCCM, 361-221, Yurim B/D, Hongie-1-dong, Seodaemun-gu, Seoul, Korea) on Feb. 24, 2010. The insertion of two copies of the putA gene in tandem was identified using PCR using a set of primers (SEQ ID NOs. 5 and 6) which targeted nucleotide sequences upstream and downstream of the two copies of the putA gene.

```
SEQ ID NO. 5:   CGAACTACGTGGCACAGTTTG
SEQ ID NO. 6:   AGCAGGCCATTAAAACGACC
```

Example 3

XMP Production of the putA-Inserted Strain

The XMP-producing strain *Corynebacterium ammoniagenes* KCJ-1346 prepared in Example 2 was cultured to produce XMP as follows. The mother strain *Corynebacterium ammoniagenes* KCCM10530 and the strain KCJ-1346 were inoculated into respective 14 mL tubes, each containing 3 mL of the following seed medium, and incubated at 30° C. for 20 hours with shaking at 200 rpm. Then, the seed cultures were added in an amount of 0.4 mL to 32 mL of the following production medium (24 mL of main medium+8 mL of additional medium) in respective 250 mL corner-baffle flasks, followed by shake culturing at 30° C. and 230 rpm for 96 hours. Thereafter, the production of 5'-xanthosine monophosphate was quantitatively measured using HPLC. The XMP amounts produced from *Corynebacterium ammoniagenes* KCCM10530 and KCJ-1346 are given in Table 1, below.

TABLE 1

| | Strain | |
|---|---|---|
| | KCCM10530 | KCJ-1346 |
| (g/L) | 28.6 | 29.9 |

Seed Medium: glucose 30 g/L, peptone 15 g/L, yeast extract 15 g/L, NaCl 2.5 g/L, urea 3 g/L, adenine 150 mg/L, guanine 150 mg/L (pH 7.2)

Production Medium (main medium): glucose 80 g/L, magnesium sulfate 10 g/L, ferrous sulfate 20 mg/L, zinc sulfate 10 mg/L, manganese sulfate 10 mg/L, adenine 30 mg/L, guanine 30 mg/L, biotin 100 μg/L, copper sulfate 1 mg/L, thiamine chloride 5 mg/L, calcium chloride 10 mg/L (pH 7.2)

Production Medium (additional medium): monopotassium phosphate 10 g/L, dipotassium phosphate 10 g/L, urea 7 g/L, ammonium sulfate 5 g/L As shown in Table 1, KCJ-1346 was found to increase the XMP production by 1.3 g/L, corresponding to 4.5% increase, compared to the mother strain KCCM10530.

Example 4

Proline Dehydrogenase Activity of putA-Inserted Strain

The XMP-producing *Corynebacterium ammoniagenes* KCJ-1346 prepared in Example 2 was assayed for proline dehydrogenase activity as follows. The strain was inoculated into a medium containing 10 g/L of bactopeptone, 5 g/L of bacto-beef extract, 5 g/L of bacto-yeast extract, 2.5 g/L of NaCl, 50 mg/L of adenine, and 50 mg/L of guanine, and incubated at 30° C. for 12 hours until OD 10 was obtained. 10 mL of the cell culture was recovered, washed twice with a buffer comprising 50 mM HEPES, 10 mM potassium acetate, 10 mM $CaCl_2$ and 10 mM $MgCl_2$, and suspended in 1 mL of 100 mM Tris-HCl buffer (pH 7.5).

After disruption using a sonicator, the cell lysate was centrifuged to separate the supernatant. The supernatant was re-centrifuged to give a pellet which was then suspended in 100 µL of buffer. 10 µL of this suspension was used as an enzyme solution. A reaction buffer was prepared by mixing 100 mM Tris-HCl (pH 7.5) and 50 µM 2,6-dichloroindolphenol ($Cl_2Ind$)). $Cl_2Ind$ was thawed and mixed just before reaction. To 980 µL of the reaction mixture were added 10 µL of 100 mM proline as a substrate and 10 µL of the enzyme solution, followed by incubation at 30° C. for 15 minutes with shaking. The enzyme activity was determined by measuring the concentration of reduced $Cl_2Ind$. $Cl_2Ind$ had an absorption coefficient of 22 $cm^{-1}$ $mM^{-1}$ at 600 nm.

TABLE 2

| | Strain | |
|---|---|---|
| | KCCM10530 | KCJ-1346 |
| Reduced $Cl_2Ind$ (µM) | 4.09 | 5.00 |

As shown in Table 2, KCJ-1346 was observed to increase proline dehydrogenase activity by 22%, compared to the mother strain KCCM10530.

Example 5

ATP Level in the putA-Inserted Strain

The XMP-producing strain *Corynebacterium ammoniagenes* KCJ-1346 prepared in Example 2 was measured for intracellular ATP level as follows.

The mother strain *Corynebacterium ammoniagenes* KCCM10530 and the mutant KCJ-1346 were inoculated into respective 14 mL tubes, each containing 3 mL of the following seed medium, and incubated at 30° C. for 20 hours with shaking at 200 rpm. Subsequently, the seed cultures were added in an amount of 0.4 mL to 25 mL of the seed medium in respective 250 mL corner-baffle flasks, followed by shake-culture at 30° C. and 230 rpm for 20 hours. Thereafter, the cell cultures were measured for OD and intracellular ATP levels.

As a result, the mutant KCJ-1346 of the present invention was found to produce ATP at a high rate per OD, compared to the mother strain KCCM10530, indicating that the mutant strain of the present invention might show high XMP and GMP productivities, compared to the known strains. The results are shown in Table 3, below.

TABLE 3

| Strain | OD (A562) | ATP Level (µM) | ATP production per OD (ATP Level/OD) |
|---|---|---|---|
| KCCM10530 | 17.3 | 37.54 | 2.17 |
| KCJ-1346 | 18.5 | 64.24 | 3.48 |

As shown in Table 3, the intracellular ATP level per OD of KCJ-1346 was increased by approximately 60%, compared to that of the mother strain KCCM10530.

Example 6

XMP Fermentation and GMP Production of the putA-Inserted Strain

The XMP-producing strain *Corynebacterium ammoniagenes* KCJ-1346 prepared in Example 2 was cultured to produce GMP as follows.

The mother strain *Corynebacterium ammoniagenes* KCCM-10530 and the mutant KCJ-1346 were inoculated into respective 14 mL tubes, each containing 3 mL of the following seed medium, and incubated at 30° C. for 20 hours with shaking at 200 rpm. Then, the seed cultures were added in an amount of 0.4 mL to 32 mL of the following production medium (24 mL of main medium+8 mL of additional medium) in respective 250 mL corner-baffle flasks, followed by shake culturing at 30° C. and 230 rpm for 96 hrs. For conversion of the produced XMP into GMP, the following conversion additives and *E. coli* XMP aminase were added to the fermentation liquid in Erlenmeyer flasks, and then a conversion reaction was conducted at 40° C. for 2.5 hours.

As a result, the mutant KCJ-1346 of the present invention was found to increase the conversion rate, which accounts for GMP production per consumed XMP, compared to the mother strain KCCM10530. Consequently, the mutant strain of the present invention showed improvement in GMP productivity, compared to the conventional strains. The results are shown in Table 4, below.

TABLE 4

| Strain | Concentration (g/L) | | Conversion Rate (%) (GMP produced/XMP consumed) |
|---|---|---|---|
| | XMP | GMP | |
| KCCM10530 | 24.7 | 17.78 | 72.0 |
| KCJ-1346 | 25.9 | 19.02 | 73.4 |

As shown in Table 4, KCJ-1346 was found to increase the conversion rate by 1.4% p and the GMP level by 6.9%, compared to the mother strain KCCM10530.

Seed Medium: glucose 30 g/L, peptone 15 g/L, yeast extract 15 g/L, NaCl 2.5 g/L, urea 3 g/L, adenine 150 mg/L, guanine 150 mg/L (pH 7.2)

Production Medium (main medium): glucose 80 g/L, magnesium sulfate 10 g/L, ferrous sulfate 20 mg/L, zinc sulfate 10 mg/L, manganese sulfate 10 mg/L, adenine 30 mg/L, guanine 30 mg/L, biotin 100 μg/L, copper sulfate 1 mg/L, thiamine chloride 5 mg/L, calcium chloride 10 mg/L (pH 7.2)

Production Medium (additional medium): monopotassium phosphate 10 g/L, dipotassium phosphate 10 g/L, urea 7 g/L, ammonium sulfate 5 g/L Conversion Additive: phytic acid 1.8 g/L, MgSO$_4$ 4.8 g/L, nymeen 3 ml/L, xylene 2%, adenine 100 mg/L, Na$_2$HPO$_4$ 7.7 g/L, glucose 46 g/L.

Effect of the Invention

Owing to improved activity of proline dehydrogenase, the *Corynebacterium* microorganism of the present invention is able to produce XMP or GMP in a much higher yield than the conventional XMP and GMP-producing microorganisms. Thus, XMP or GMP can be produced in a high yield using the microorganism of the present invention.

What is claimed is:

1. A *Corynebacterium* microorganism for producing 5'-xanthosine monophosphate or 5'-guanosine monophosphate, having increased proline dehydrogenase activity as compared to its endogenous activity, wherein the proline dehydrogenase activity is increased by enhancing the expression level of a putA ene of *Corynebacterium*.

2. The *Corynebacterium* microorganism according to claim 1, wherein the putA gene has a nucleotide sequence of SEQ ID NO. 7.

3. The *Corynebacterium* microorganism according to claim 1, wherein the microorganism is transformed by introduction of a vector comprising a putA gene.

4. The *Corynebacterium* microorganism according to claim 1, wherein the microorganism has improved ATP productivity.

5. The *Corynebacterium* microorganism according to claim 1, wherein the microorganism is *Corynebacterium ammoniagenes*.

6. The *Corynebacterium* microorganism according to claim 1, wherein the microorganism is identified by Accession No. KCCM11068P.

7. A method for producing 5'-xanthosine monophosphate (XMP), comprising:
(a) culturing the microorganism of claim 1; and
(b) obtaining 5'-xanthosine monophosphate from the culture solution of step (a).

8. A method for producing 5'-xanthosine monophosphate according to claim 7, wherein the putA gene has a nucleotide sequence of SEQ ID NO. 7.

9. A method for producing 5'-xanthosine monophosphate according to claim 7, wherein the microorganism is *Corynebacterium ammoniagenes*.

10. A method for producing 5'-guanosine monophosphate, comprising
    (a) culturing the microorganism of claim 1;
    (b) adding 5'-xanthosine monophosphate aminase to the culture solution of the strain obtained in step (a); and
    (c) obtaining 5'-guanosine monophosphate from the culture solution of step (b).

* * * * *